United States Patent [19]

Butera et al.

[11] Patent Number: 5,256,534

[45] Date of Patent: Oct. 26, 1993

[54] CD4+, LATENTLY HIV-1-INFECTED HEMATOPOIETIC PROGENITOR CELLS

[75] Inventors: Salvatore T. Butera, Stone Mountain; Thomas M. Folks, Lithonia, both of Ga.; Victor L. Perez, Rio Piedras, Puerto Rico

[73] Assignee: The United States of America as represented by the Department of Health and Human Services, Washington, D.C.

[21] Appl. No.: 742,750

[22] Filed: Aug. 9, 1991

[51] Int. Cl.$^5$ ............................................. C12Q 1/70
[52] U.S. Cl. ............................................ 435/5; 435/8; 435/7.24; 435/239; 435/240.26
[58] Field of Search ................. 435/240.26, 239, 5, 435/7.24

[56] References Cited

PUBLICATIONS

Clouse et al: Monokine Regulation . . . Human T cell clone (TR) vol. 142, J. Immunol Jan. 1989 pp. 431–438.
Folks et al: Infection & Replication . . . Bone Marrow (UR) Science vol. 242 pp. 919–922 Nov. 1988.
Stedman's Medical Dictionary, 25th Ed., p. 1276 (1990).
Thomas M. Folks, et al., Biological and Biochemical Characterization of a Cloned Leu-3$^-$ Cell Surviving Infection with the Acquired Immune Deficiency Syndrome Retrovirus, vol. 164, Jul. 1986 280–290.
Thomas M. Folks, et al., Cytokine-Induced Expression of HIV-1 in a Chronically Infected Promonocyte Cell Line. vol. 238.
Thomas M. Folks, et al., Characterization of a Promonocyte Clone Chronically Infected with HIV and Inducible by 13-Phorbol-12-Myristate Acetate, vol. 140, 1117–1122, No. 4, Feb. 15, 1988.
M. I. Bukrinsky, et al., Quiescent T Lymhocytes as an Inducible Virus Reservoir in HIV-1 Infection. 10 Oct. 1991.

Primary Examiner—Christine M. Nucker
Assistant Examiner—Jeffrey Stucker
Attorney, Agent, or Firm—Susan S. Rucker

[57] ABSTRACT

The present invention relates to a unique physiologic model of chronic human immunodeficiency virus type-1 (HIV-1) infection. In particular, the present invention relates to a chronically infected promyelocyte cell line harboring a single integrated provirus. Unlike other models of chronic infection, the cell line of the present invention remain CD4+ under normal culture conditions during which <10% of the cells constitutively express HIV-1 proteins. However, when treated with tumor necrosis factor-alpha (TNF-$\alpha$), the cell line dramatically increased (>35-fold) HIV-1 expression and rapidly down-modulated surface CD4, as >95% of the cells became HIV-1+. These results with the new OM-10.1 cell line demonstrate that CD4 surface expression can be maintained during chronic infection and is critically dependent upon the state of viral activation; that CD4-gp160/120 intracellular complexing is responsible for CD4 down-modulation; and that protein kinase pathways function not only in the primary induction of latent HIV-1 but are also involved in maintaining the state of viral activation.

10 Claims, 15 Drawing Sheets

+ TNF-α @ 20 U per ml

T-0  4h  8h  12h  18h  24h  36h  48h

+ PMA @ $10^{-7}$ M

T-0  4h  8h  12h  18h  24h  36h  48h

+ TNF-α @ 100 U per ml

T-0  4h  8h  12h  18h  24h  36h  48h

+ PMA @ $10^{-7}$ M

T-0  4h  8h  12h  18h  24h  36h  48h

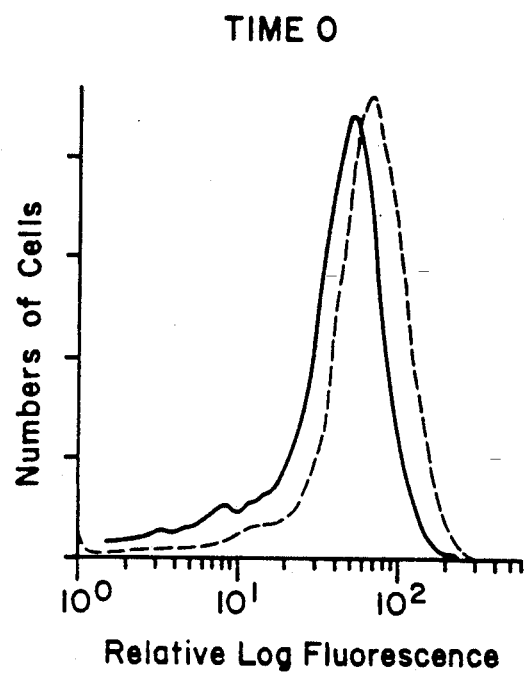
FIG. 6A1
TIME 0
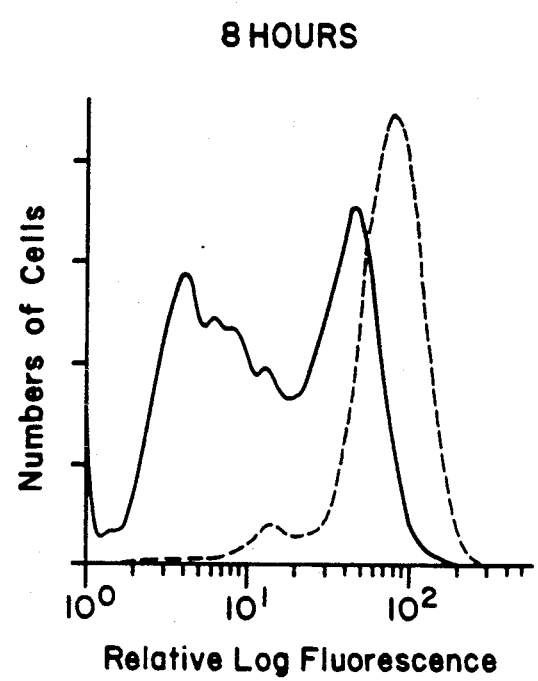
FIG. 6A2
8 HOURS
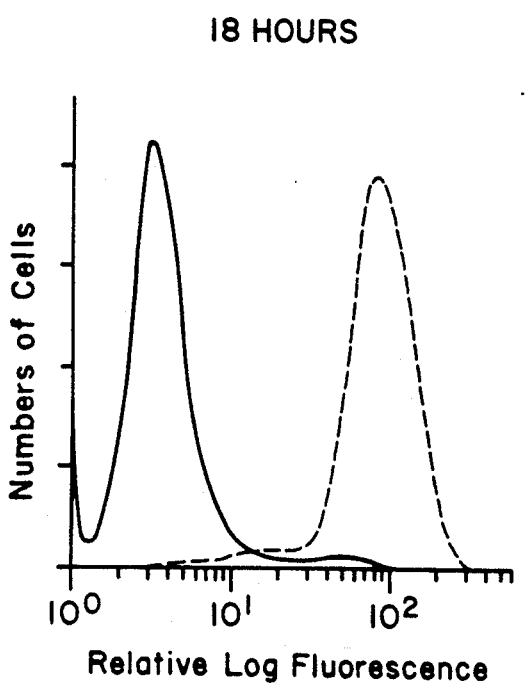
FIG. 6A3
18 HOURS
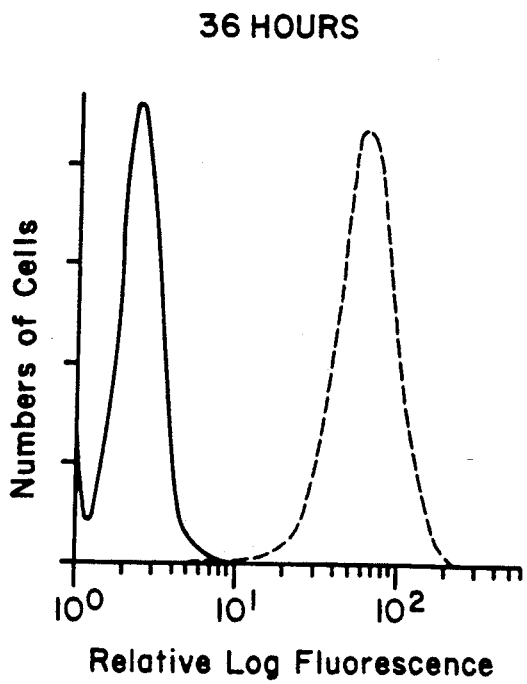
FIG. 6A4
36 HOURS

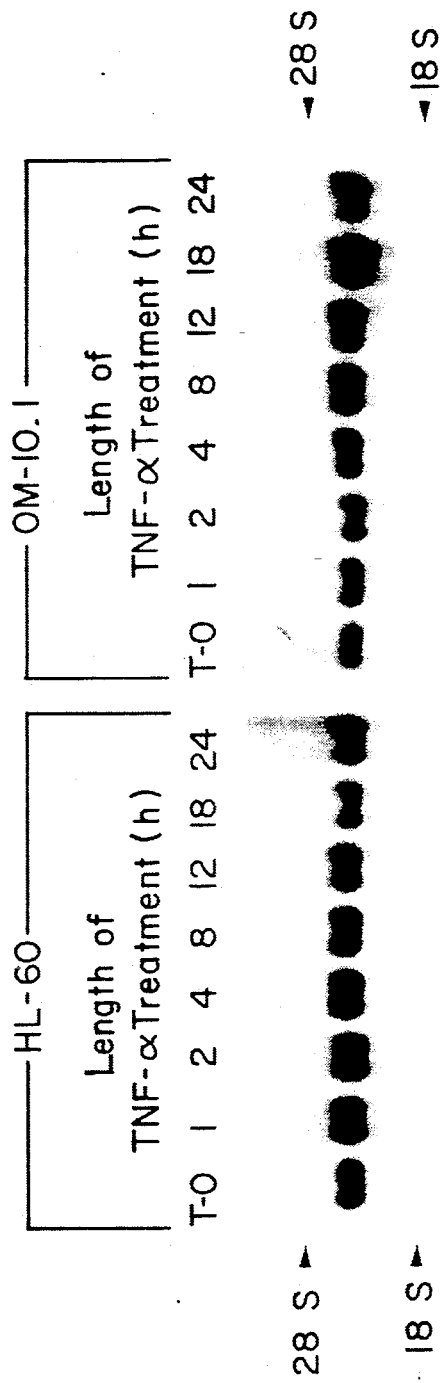

FIG. 7A anti-CD4
Precipitated
T-0  12 h  36 h

▲ 200 kDa

▲ 96

▲ 69

Immunoblot analysis
with pooled AIDS sera

FIG. 7B anti-gp120
Precipitated
T-0  12 h  36 h

▼ 200 kDa

▼ 96

▼ 69

Immunoblot analysis
with pooled AIDS sera

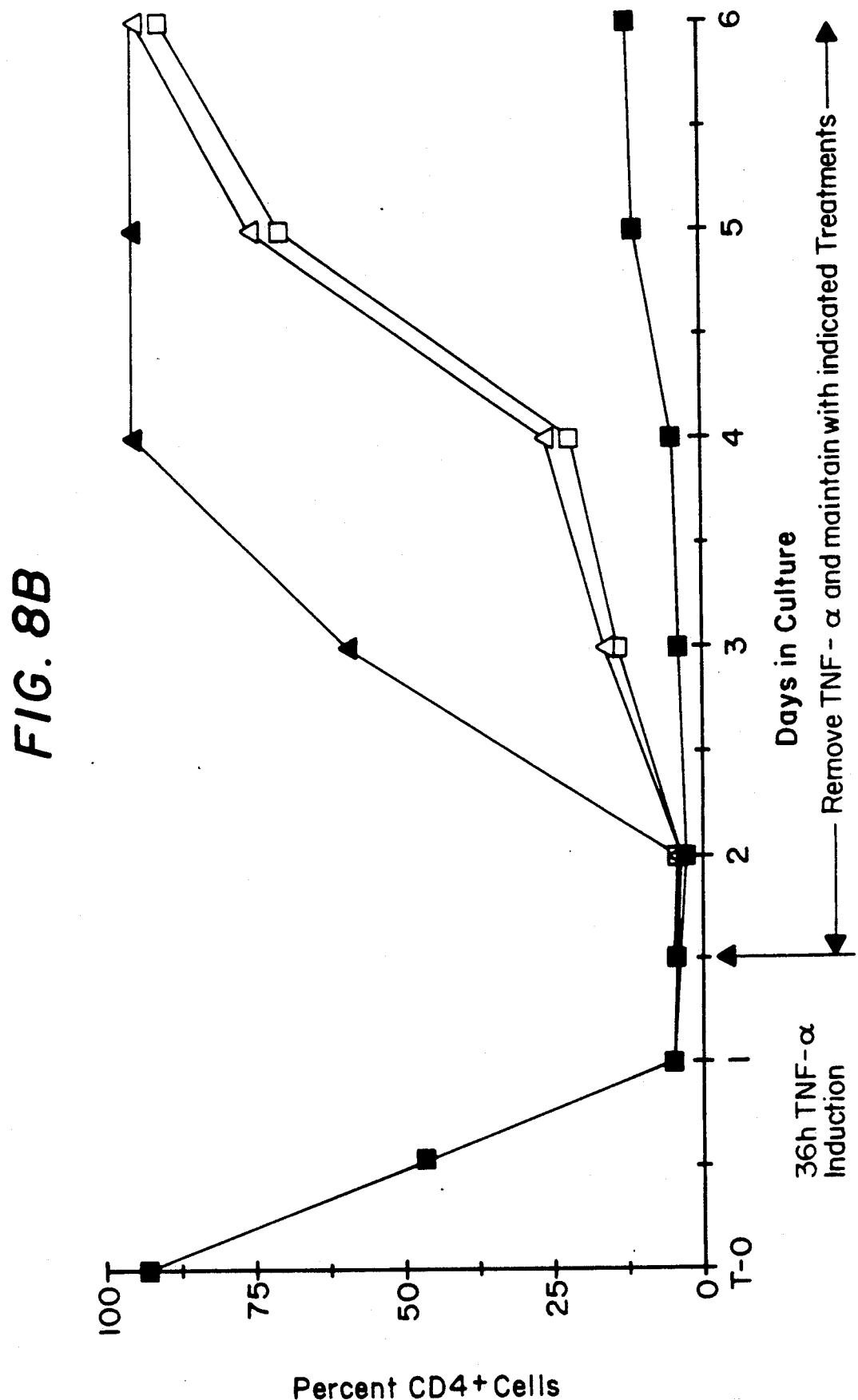

CD4+, LATENTLY HIV-1-INFECTED HEMATOPOIETIC PROGENITOR CELLS

BACKGROUND OF THE INVENTION

1. Field of the Invention

The present invention relates to a latently-infected HIV-1 hematopoietic cell which maintains surface expression of CD4. The present invention further relates to methods of identifying anti-HIV-1 agents.

2. Background Information

The AIDS epidemic is a pressing health issue both in the United States and abroad. The retrovirus human immunodeficient virus type-1 (HIV-1) is the causative agent of AIDS. During the course of the AIDS disease there is normally an initial period of clinical latency which can extend for several years after infection with HIV-1 (Fauci, A. S. 1988, Science (Wash. D.C.), 239:617–622; Ranki et al., 1987, Lancet ii:589–593). During this period, HIV-1 may exist as a dormant or non-expressing provirus in a reservoir population of chronically infected cells (Hoxie et al., 1985, Science 229:1400–1402).

In Vitro studies with chronically HIV-1-infected tumor cell lines have shown that activation of the dormant provirus occurs when the correct stimuli are encountered (Clouse et al., 1989, J. Immunol. 142:431–438; Folks et al., 1987, Science 238:800–802; Folks et al., 1988, J. Immunol. 140:1117–1122; Folks et al., 1989, Proc. Natl. Acad. Sci. USA 86:2365–2368). Theoretically, a similar activation occurs with chronically infected cells in vivo and results in CD4 down-modulation, production of viral progeny, and cytopathic sequela (Fauci, A. S. 1988, Science (Wash. D.C.) 239:617–622).

The CD4+ T lymphocyte is the in vivo reservoir for HIV-1 (Psallidopoulos et al., 1989, J. Virol. 63:4626–4631; Schnittman et al., 1989, Science (Wash. D.C.) 245:305–308). Accordingly, CD4 surface expression apparently can be maintained during viral latency and expression of the virus is necessary to cause CD4 down-modulation. During HIV-1 expression, intracellular HIV-1 gp160/120-CD4 complexing (Crise et al., 1990, J. Virol. 64:5585-5593; Kawamura et al., 1989, J. Virol. 63:3748-3754; Koga et al., 1990, J. Virol. 64:4661-4671) and disruption of CD4 transcription (Hoxie et al., 1986, Science (Wash. D.C.) 234:1123-1127; Salmon et al., 1988, J. Exp. Med. 168:1953-1969) or translation (Yuille et al. 1988, J. Acquired Immune Defic. Syndr. 1:131-137) have been observed to explain this effect on surface CD4 levels. In addition, intracellular HIV-1 gp160/120-CD4 complexing has been implicated by some as a mechanism of viral cytopathicity (Hoxie et al., 1986, Science (Wash. D.C.) 234:1123-1127; Koga et al., 1990, J. Virol. 64:4661-4671), while other investigators have shown the cytopathic effect to be dependent upon the level of CD4 expression by the target cells (Koga et al., 1990, J. Immunol. 144:94-102; Rossi et al., 1986, Proc. Natl. Acad. Sci. USA. 83:4297-4301).

Although these facts are well established, it remains uncertain why CD4 expression is lost from the surface of chronically HIV-1 infected cell lines since they constitutively express only minimal amounts of HIV-1 proteins (Clouse et al., 1989, J. Immunol. 142:431-438; Folks et al., 1988, J. Immunol. 140:1117-1122; Hoxie et al., 1985, Science 229:1400-1402; Stevenson et al., 1987, J. Virol. 61:3741-3748). The inability of chronically HIV-1 infected cell lines to maintain surface CD4 expression has made them less than ideal modes of HIV-1 latency and unusable systems to explore the molecular mechanisms involved in CD4 modulation by HIV-1. The development of a latently HIV-1-infected cell model is critical for a full understanding of the virus and for the development of vaccines and therapeutic treatments. Such a cell model would ideally reproduce the HIV-1 induced CD4 modulation and serve as a physiologic model of the in vivo HIV-1 reservoir.

SUMMARY OF THE INVENTION

Accordingly, it is one object of the present invention to provide a chronically HIV-1-infected cell which mimics the physiologic HIV-1 latency in the body.

It is another object of the present invention to provide an HIV-1-infected pluripotent hematopoietic progenitor cell which can be differentiated into several terminal phenotypes.

It is a further object of the present invention to provide a means of conducting biological and pharmaceutical studies of the HIV-1 infection and methods of preventing activation from latency.

Various other objects and advantages of the present invention will become apparent from the following detailed description thereof.

In one embodiment, the present invention relates to a CD4+ hematopoietic cell comprising an HIV-1 provirus.

In another embodiment, the present invention relates to a method of identifying and rapidly testing novel anti-HIV-1 agents and strategies. In one such method cells of the present invention are contacted with a test agent and the presence or absence of cell death detected. In another such method, agents which prevent HIV-1 activation from latency are identified by contacting said cells according to claim 1 with said agent and an HIV-1 activation stimulus, and detecting the presence or absence of HIV-1 activation.

BRIEF DESCRIPTION OF THE DRAWINGS

FIGS. 7A and 7B show the combined immunoprecipitation and immunoblot analysis of OM-10.1 cell lysates for the detection of intracellular HIV-1 gp160/120-CD4 complexes. Lysates were used from uninduced OM-10.1 cells (T-0) and after 12 h or 36 h of TNF-α treatment. These lysates were immunoprecipitated with either anti-CD4 (OKT4) (left panel) or anti-gp120 monoclonal antibodies (right panel) and then immunoblotted for HIV-1-specific proteins with pooled AIDS sera. Molecular weight markers (kDa) are as indicated. Based on the migration of the immunoprecipitate band in relation to the molecular weight markers, it appears that CD4-gp160 is the major intracellular complex.

DETAILED DESCRIPTION OF THE INVENTION

Figure 1:
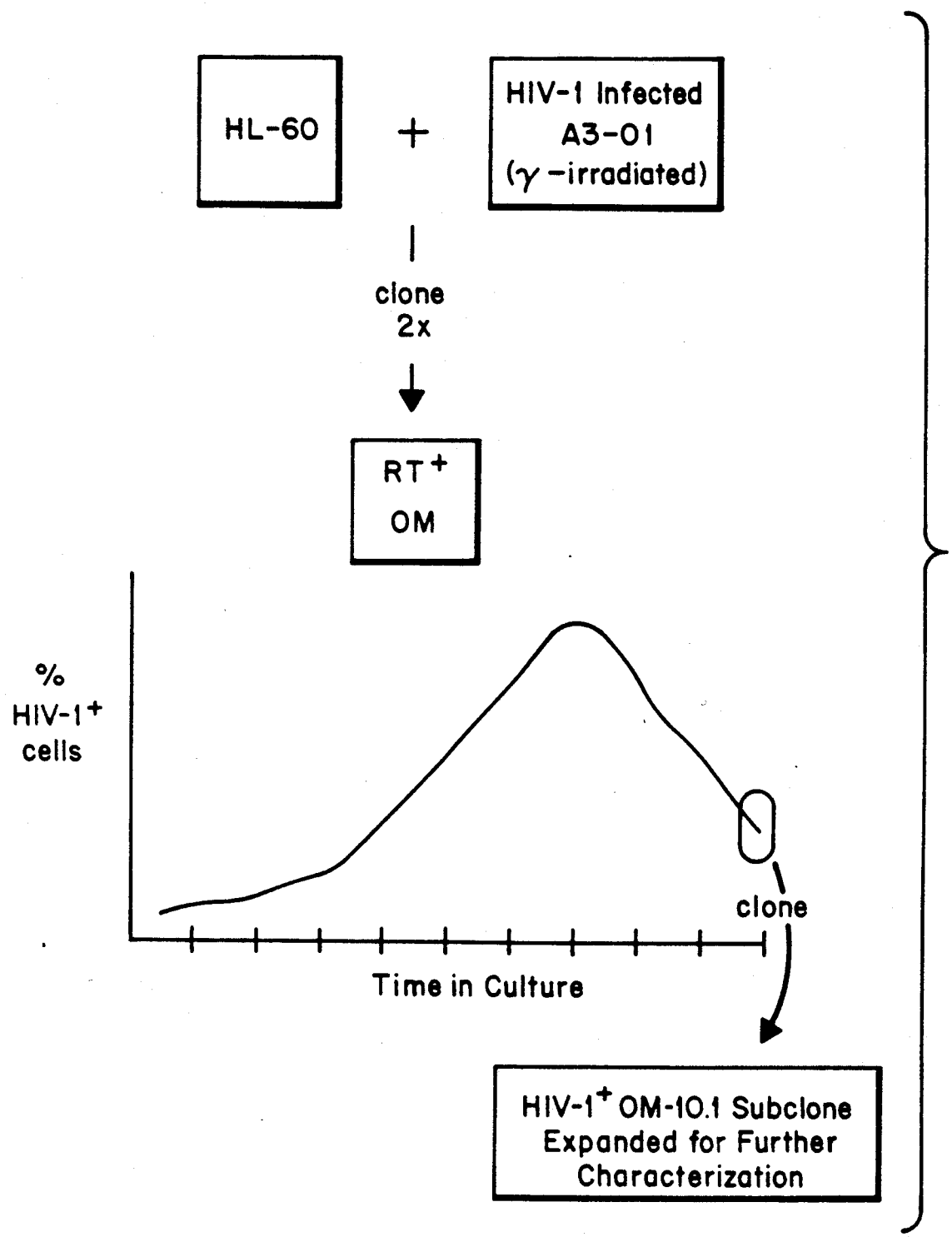
FIG. 1 shows schematically the derivation of the OM-10.1 clone. Normal HL-60 promyelocytes were infected by coculturing with HIV-1 (LAV) infected, τ-irradiated A3-01 cells. Following the acute infection which insued, surviving cells were subcloned to derive a pure clonal population.

The present invention relates to a pluripotent hematopoietic cell latently infected with a HIV-1 provirus. In particular, the present invention relates to the latently infected bone marrow progenitor cell which maintains CD4 expression on the cell surface. The present invention also relates to methods of producing the HIV-1 proteins and to methods of rapidly identifying novel anti-HIV-1 agents.

In one embodiment, the present invention relates to a hematopoietic cell (preferably a pluripotent progenitor cell, more preferably a promyelocytic cell), which is latently infected with a HIV-1 provirus and maintains surface expression of CD4. The present invention is exemplified by the promyelocyte cell line, OM-10.1.

While OM-10.1 is a promyelocyte, one skilled in the art will recognize that the present invention relates to pluripotent bone marrow stem cells and cells differentiated therefrom which are latently infected with the HIV-1 provirus and which retain CD4 expression. In addition to promyelocytes, the present invention also related to differentiated bone marrow cells such as, for example, neutrophils, basophils, monocytes, macrophages and eosinophils. Such cells which are latently-infected with HIV-1 can be produced by applying growth or differentiation factors to pluripotent stem cells of the present invention under conditions such that cell differentiation occurs. For example, infected OM-10.1 cells can be differentiated into terminal phenotypes to produce HIV-1 latently infected neutrophils. Such infected neutrophils are difficult or unfeasible to obtain using standard infection methods. Thus, provides models to study the influence of HIV-1 expression in terminal hematopoetic cell types.

Due to its expression of surface CD4, cells of the present invention provide a physiological model of chronic HIV-1 infection. Unlike other models of HIV-1 infection, under normal culture conditions CD4 surface expression on the cells is maintained during chronic infection and is dependent upon the state of viral activation. Surface expression of CD4 declines upon HIV-1 activation and accumulation. Thus, treatment of the cells with a viral stimulus, such as, TNF-α or phorbol esters, increases HIV-1 expression and, at the same time, down-modulates CD4 expression. Further, once HIV-1 activation has ceased, surface expression of CD4 returns.

In a patient infected with HIV-1 there is normally an initial period of clinical latency during which time the virus exists as non-expressing provirus in a reservoir population of chronically infected cells. During the course of the disease, infected cells periodically begin to express HIV-1, possibly due to extracellular stimuli. Activation of HIV-1 from latency results in the maintenance and spread of HIV-1 to other suspectable cells in the body. OM-10.1 provides a physiologic model of such a chronic HIV-1 infection as the cells provide a CD4+ reservoir of HIV-1 which can be stimulated to express HIV-1. In addition, withdrawal of the stimulus results in the cells returning to their CD4+ phenotype and remain as a potential target for HIV-1 superinfection or reactivation. Thus, the oscillation of the cell line between virus production and CD4 expression enables those in the art to study the mechanisms controlling nonproductive chronic infection, activation from latency and treatments for the infection.

The cells of the present invention further serve as a model of HIV-1 superinfection. Infection of a patient with HIV-1 can lead to either destruction of the host cell or to a persistant, noncytopathic infection of CD4+ lymphocytes and monocytes. During acute infection in vitro, the accumulation of unintegrated viral DNA due to superinfection results in an acute, cytopathic effect on the host cell. In contrast, significant amounts of unintegrated viral DNA are not generally observed in persistent HIV-1 infections in vivo, probably due to CD4 down-modulation by the cell lines thus far developed.

Superinfection occurs when cells already harboring an integrated provirus are further infected with unintegrated copies of the HIV-1 virus. When superinfection occurs, the unintegrated virus can activate the latent provirus or replicate extrachromosomally and contribute to the cytopathic sequela. In contrast to other models of chronic infection, the cells of the present invention containing the HIV-1 provirus can be rapidly and conveniently superinfected with HIV-1 due to maintained surface CD4 expression. Little or no cytopathicity is observed during unintegrated HIV-1 DNA accumulation in OM-10.1 cells in contrast to observations in previous studies with other in vitro retroviral systems involving acute infections (Keshel et al., 1979, J. Virol. 31:376-388, Weller et al., 1980, J. Virol. 33:494-506). The cells of the present invention, thus, provide a means of studying HIV-1 superinfection and the oscillation between HIV-1 latency and HIV-1 activation induced by superinfecting virion.

The cells of the present invention also provide a source of HIV-1 protein antigens, such as, p24, core antigen and gp120 envelope glycoprotein. Currently, the 8E5 cell line (JEM 164:280, 1986) serves as the resource for large commercial production of HIV-1 protein antigens. However, the cells of the present invention offer several advantages which are not obtained with the 8E5 cells. First, the 8E5 cell line produces pol gene mutant virions whereas the OM-10.1 cell line appears to produce a wild-type (or slightly attenuated) virions. Moreover, the 8E5 cells do not synthesize all the HIV-1 viral proteins, in contrast with the OM-10.1 cells which produce all viral proteins of the correct molecular size. Furthermore, 8E5 cells undergo fluctuations of viral expression and non-producing clones arise. Over more than a year, no such non-producing clones have been observed in OM-10.1 cultures after stimulation and the response of these cells remains high.

In another embodiment, the present invention relates to a method of identifying anti-HIV-1 agents (for example, anti-HIV-1 drugs). Using the cells of the present invention, agents can be tested for their ability to selectively destroy the infected cells using standard methods in the art. In addition, agents which suppress HIV-1 activation from the latent stage can be rapidly and conveniently identified. To test for agents which prevent activation of the latent virus, cells of the present invention can be contacted with the agent and an HIV-1 activation stimulus. Within 24 hours, effective agents will prevent the down-modulation of CD4 and increase in HIV-1 expression which can be detected using standard methods known in the art. Large numbers of potential agents can be screened simultaneously.

The following non-limiting examples are given to further demonstrate the present invention.

EXAMPLES

The following protocols and experimental details are referenced in the examples that follow:

Cell Lines and Culture Conditions

HL-60 (Collins, S. J., 1987, Blood 70:1233–1244), OM-10.1, and 8E5 (Folks et al., 1986, J. Exp. Med. 164:280–290) cell lines were maintained in RPMI 1640 basal medium (GIBCO, Grand Island, N.Y.) containing 10% fetal bovine serum, 2 mM glutamine, and 1% Pen-Strep (GIBCO) at 37° C. in a humidified atmosphere of 5% $CO_2$ and 95% air. Mycoplasma-free OM-10.1 cell cultures were established and, in general, showed no biologic differences compared with the original OM-10.1 cultures. HIV-1 expression was induced from OM-10.1 cells by treatment with either 20 U/ml rTNF-$\alpha$ (Genzyme Corp., Boston, Mass.) or 0.1 $\mu$M phorbol-12-myrisate-13-acetate (PMA, Sigma Chemical Co., St. Louis, Mo.). All induction experiments were performed at a concentration of $5 \times 10^5$ cells/ml for a maximum of 36 h. In experiments were protein kinase inhibitors were used, H7 (1-[5-isoquinolinesulonyl]-2-methylpiperazine hydrocholoride) and HA1004 (N-[2-guanidinoethyl]-5-isoquinolinesulfonamide hydrochloride) (Seikagaku America, Inc., Rockville, Md.) were added to a final culture concentration of 16.67 $\mu$M.

Quantitation of HIV-1 Expression

HIV-1 expression was quantitated by reverse transcriptase (RT) enzymatic activity. As described (Willey et al., 1988, J. Virol. 62:139–147), 5 $\mu$l cell-free culture supernatant was added to 25 $\mu$l of "RT cocktail" containing polyadenylate oligo(dT) (Pharmacia Fine Chemicals, Piscataway, N.J.), $MgCl_2$, and [$\alpha$-$^{32}$P]-dTTP (Amersham Corporation, Arlington Heights, Ill.) in duplicate wells of a U-bottom 96-well plate and incubated at 37° C. for 2 h. Five microliters of this mixture was then spotted onto DE81 ion exchange chromatography paper (Whatman International, Madison, England), air-dried, washed five times in 1.5$\times$ SSC (1$\times$ SSC is 15 mM sodium citrate plus 150 mM NaCl), and twice more with 95% ethanol. The paper spots were then dried and the remaining radioactivity was quantitated in a Beckman LS 7000 scintillation counter. HIV-1 expression was also quantitated by p24 antigen-specific enzyme linked immunosorbent assay (ELISA) (Maryland Medical Laboratories, Inc., Baltimore, Md.) of cell culture supernatant, following the manufacturer's protocol.

Cells were examined directly for HIV-1 expression by immunofluorescence assay, using an fluorescein isothiocyanate-conjugated, partially purified, polyclonal anti-HIV-1 antiserum (prepared from serum of an AIDS patients and provided by S. McDougal, CDC). Cells were first attached to Adhesio Slides (MM Developments, Ottawa, Ont., Canada) and then fixed in 4° C. acetone. Cell fields were nonspecifically blocked with 5% normal goat serum and then reacted with a 1:50 anti-HIV-1 antiserum solution; both were prepared with the buffer used for flow cytometric analysis (see below). After 45 minutes at room temperature, the slides were rinsed with phosphate-buffered saline (PBS) (10 mM $NaH_2HPO_4$, 150 mM NaCl [pH=7.4]) and examined by UV microscopy.

Determination of CD4 Expression

Cells were washed once in cold PBS and once in cold PBS containing 2% normal human AB+serum, 0.2% sodium azide and 0.1% BSA (FACS buffer). Cell pellets were resuspended in 75 μl FACS buffer containing 12.5 μl of anti-CD4 monoclonal antibody (OKT4, Ortho, Raritan, N.J.) or, as a negative control, anti-CD8 monoclonal antibody (OKT8, Ortho). After 1 hour at 4° C., cells were washed twice with FACS buffer and resuspended in 100 μl FACS buffer containing 2 μl of phycoerythrin-conjugated goat-anti-mouse immunoglobulin G antibody (Tago, Burlingame, Calif.). After an addition 1 hour at 4° C. cells were washed twice in FACS buffer and fixed at 4° C. with PBS containing 1% paraformaldehyde in preparation for analysis on a Becton Dickinson FACScan system. Additionally, culture supernatants were tested by ELISA for soluble CD4 shed from the cell surface, following the manufacturer's protocol (T-Cell Sciences, Cambridge, Mass.).

Southern Blotting of OM-10.1 Genomic DNA

A total of $5 \times 10^7$ cells were washed twice with cold PBS, lysed in 20 mM tris buffer containing 5 mM EDTA and 5 mg/ml sodium dodecyl sulfate, and digested with 100 μg/ml proteinase K for 5 h (Maniatis, T., E. F. Fritsch, and J. Sambrook, 1982, Molecular Cloning: a laboratory manual. Cold Spring Harbor Laboratory, Cold Spring Harbor, N.Y.). After phenol extraction, the final aqueous phase was precipitated with ethanol, resuspended in TE buffer (10 mM Tris HCl, 1 mM EDTA, pH=7.6), and quantitated by $A_{260}$. Approximately 25 μg of total genomic DNA was digested overnight with an excess of Eco-R1 and then separated through a 0.8% agarose gel. The digested DNA was transferred to a nylon membrane and then hybridized with a $^{32}$P-labeled, Eco-R1/Kpn-1 0.5 kb HIV-1 fragment of pBenn-7 (Gendelman et al., 1986, Proc. Natl. Acad. Sci. USA 83:9759-9763) for the 5' viral genome and associated host flank. Bands of hybridization were detected by autoradiography.

Immunoblotting of Cellular Lysates

Cells were washed twice in PBS and lysed in detergent buffer, as described (Tsang et al., 1983, Methods Enzymol. 92:377-391). Total protein of each lysate was quantitated by the bicinchoninic acid method, following the manufacturer's protocol (Pierce, Rockford, Ill.). One hundred micrograms of total cellular protein was separated by polyacrylamide gel electrophoresis under reducing conditions and then electrotransferred to nitrocellulose, as described (Towbin et al., 1979, Proc. Natl. Acad. Sci. USA. 76:4350-4354). HIV-1-specific proteins were detected by using a 1:100 dilution of pooled sera from AIDS patients and CD4 was detected by using a 1:1000 dilution of rabbit anti-human CD4 polyclonal antibody. Proteins bound by these primary antibodies were resolved with $^{125}$I-labeled protein G ($10^5$ cpm/ml) and autoradiography. Initial blocking, incubations, and washes were performed as described (Tsang et al., 1983, Methods Enzymol. 92:377-391).

The same cellular lysates were also used for combined immunoprecipitation and immunoblot analysis. Precleared cellular protein (150 μg) was immunoprecipitated with either anti-CD4 (OKT4) or anti-gp120 (DuPont, Billerica, Mass.) monoclonal antibodies conjugated to protein A-sepharose (Sigma). The precipitated proteins were eluted and separated by polyacrylamide gel electrophoresis under reducing conditions. After transfer to nitrocellulose, HIV-1 proteins specifically extracted by immunoprecipitation were detected by immunoblotting, as described above.

Northern Blotting of Total Cellular RNA

Following the appropriate culture conditions, cells were washed twice with cold PBS and then lysed in a guanidine thiocyanate buffer, as described (Strohman et al., 1977, Cell 10:265-273). Total RNA was purified by cesium chloride gradient ultracentrifugation and quantitated by $A_{260}$.

Ten micrograms of total purified RNA was denatured and electrophoresed through a 0.8% agarose gel containing formaldehyde. The separated RNA was then transferred to a nylon membrane (Hybond, Amersham) and probed in a 50% formamide hybridization buffer overnight at 42° C. For CD4 mRNA detection, a 2 kb cDNA probe (Maddon et al., 1986, Cell 47:333-348)and for HIV mRNA detection, a 2 kb 5'-LTR genomic probe (Bednorik et al., 1990, EMBO J. 9:1157-1164), labeled with [$\alpha$-$^{32}$P]-dCTP by random priming (Amersham), was used. After hybridization, the membranes were washed twice at 57° C. in $2 \times$ SSC plus 1% sodium dodecyl sulfate in preparation for autoradiography.

Example 1

Characterization and Induction of the OM-10.1 Clone

Figure 2A:
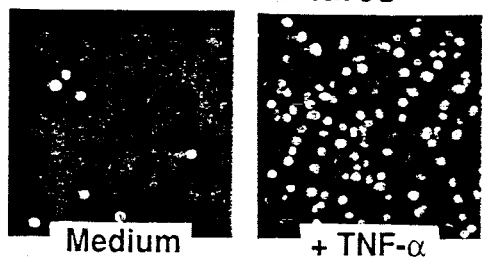
FIG. 2 demonstrates constitutive and induced HIV-1 expression by OM-10.1 cells. (A) Direct immunofluorescence assay of OM-10.1 cells maintained in medium (left panel) and treated with TNF-α for 36h (right panel) for HIV-1-specific protein expression. (B) Induction of HIV-1 expression by OM-10.1 cells after 36-h treatment with TNF-α (20 U/ml) or PMA (0.1 μM), as determined by reverse transcriptase (RT) activity of culture supernatants. Data are presented both as actual RT activity (in cpm) and as a Stimulation Index ((RT cpm of treated culture)/(RT cpm of medium culture)). Results are representative of greater than 10 separate trials.
Figure 2B:
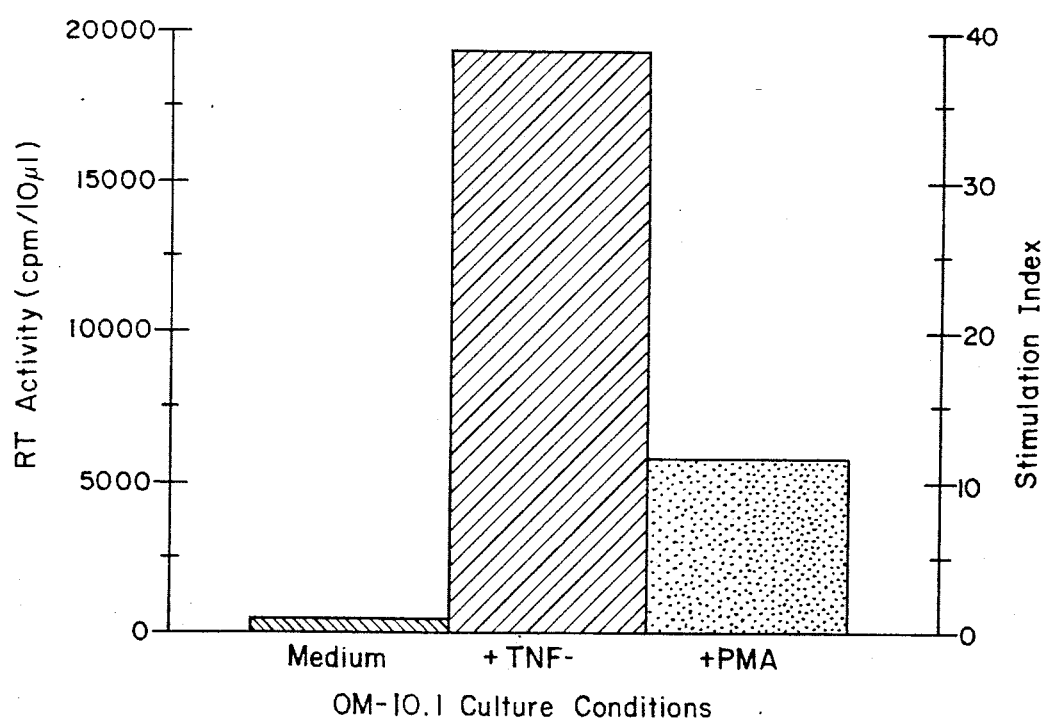

The OM-10.1 clone was derived by limit diluting the cells which survived an acute HIV-1 infection of HL-60 promyelocytes (FIG. 1). After clonal expansion, <10% of OM-10.1 cells were HIV-1+ by direct immunofluorescence (FIG. 2A) and a low level of RT activity was detected in OM-10.1 culture supernatants (FIG. 2B). By flow cytometric analysis, OM-10.1 cells expressed levels of myeloid-specific surface antigens (CD13, CD14, MY8, CD33, and CD34), HLA-A/B/C, HLA-DR, and CD71 (transferrin receptor) similar to those expressed by the parental uninfected HL-60 cells.

Because of their low constitutive HIV-1 expression, OM-10.1 cultures were treated with either TNF-α or PMA and then evaluated for induced HIV-1 expression. As measured by RT activity of culture supernatants (FIG. 2B), TNF-α treatment of OM-10.1 cells increased virus expression almost 40-fold while PMA treatment resulted in a 12-fold increase with 36 h. The induction of HIV-1 expression by OM-10.1 cultures was even more dramatic when quantitated by p24 ELISA, in which HIV-1 levels after TNF-α treatment rose 1,000-fold over background in some experiments. Directly associated with the increased HIV-1 expression, virtually 100% of the cells from TNF-α-treated OM-10.1 cultures were HIV-1+ by immunofluorescence (FIG. 2A).

Figure 3:
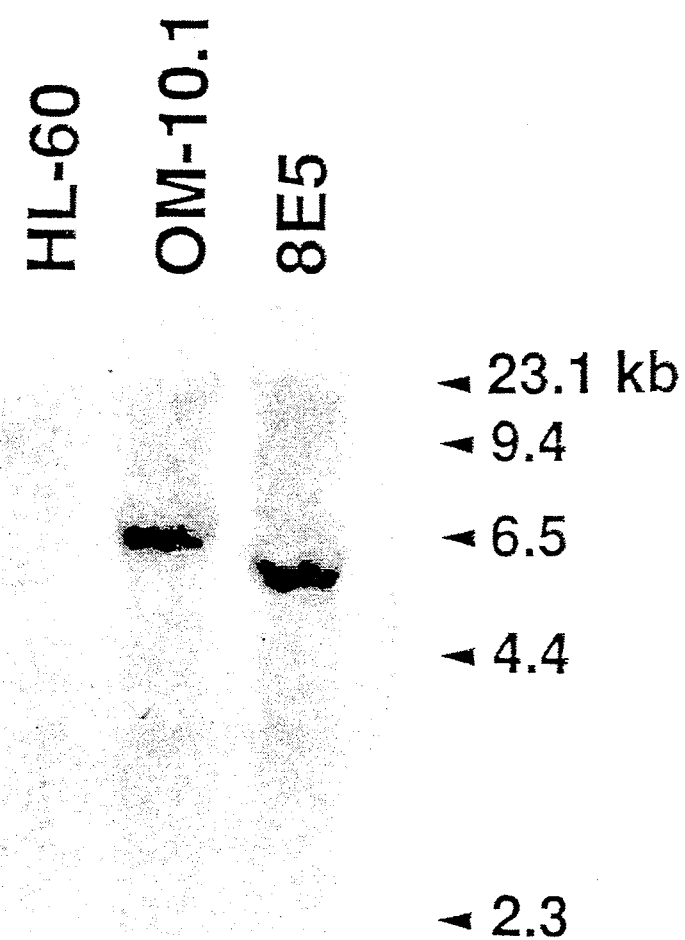
FIG. 3 shows a Southern blot analysis of Eco-R1 restricted total genomic DNA from HL-60, OM-10.1, and 8E5 cells. The restricted DNA was probed with a $^{32}$P-labeled, Eco-R1/Kpn-1 0.5 kb HIV-1 fragment for the 5' region of the HIV-1 genome and a variable region of host flank (dependent upon the integration site). The molecular weight markers (kb) are based on the migration of lambda phage DNA restricted by Hind-III digestion.
Figure 4A:
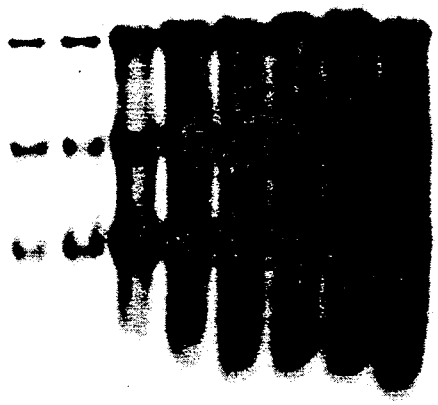
FIGS. 4A–D demonstrate the production and accumulation of HIV-1 RNA after induction of OM-10.1 and U1 cells with TNF-α and PMA. Autoradiographes were developed by standard procedures. Northern blot of total purified RNA hybridized to a $^{32}$P-labeled 5'-LTR probe.
Figure 4B:
Figure 4C:
Figure 4D:
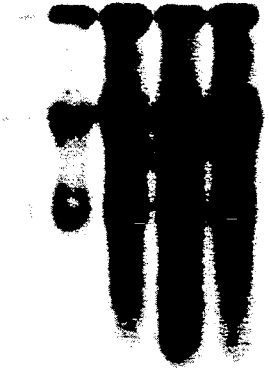

The clonal origin of the OM-10.1 cell line was confirmed by Southern analysis. Total genomic DNA was restricted by Eco R1 digestion and probed for the 5' region of the HIV-1 provirus and associated host genomic flank (FIG. 3). The DNA from OM-10.1 cells produced a distinct single band of approximately 6.5 kb when analyzed in this manner, whereas no bands were visible from HL-60 DNA. The DNA from 8E5 cells, a cloned T-cell line harboring a single HIV-1 provirus (Folks et al., 1986, J. Exp. Med. 164:280-290), also produced a single band following hybridization. These results verified the clonal derivation of the OM-10.1 line and established that these cells harbor a single integrated HIV-1 provirus.

Example 2

Pattern of Surface CD4 Expression by OM-10.1 Cells

Unexpectedly, most (>90%) uninduced OM-10.1 cells maintained surface CD4 expression at a level similar to that of uninfected parental HL-60 cells (FIGS. 6A1-A4). A small percentage of CD4- cells was evident in the uninduced OM-10.1 cultures, apparently due to the <10% HIV-1+ population observed by direct immunofluorescence. However, upon TNF-α treatment, surface CD4 expression by OM-10.1 cultures began to decrease progressively until >95% of the cells were CD4- after 36 h. TNF-α treatment of uninfected parental HL-60 cells did not alter the level of surface CD4 expression (FIGS. 6A1-A4).

Figure 6B:
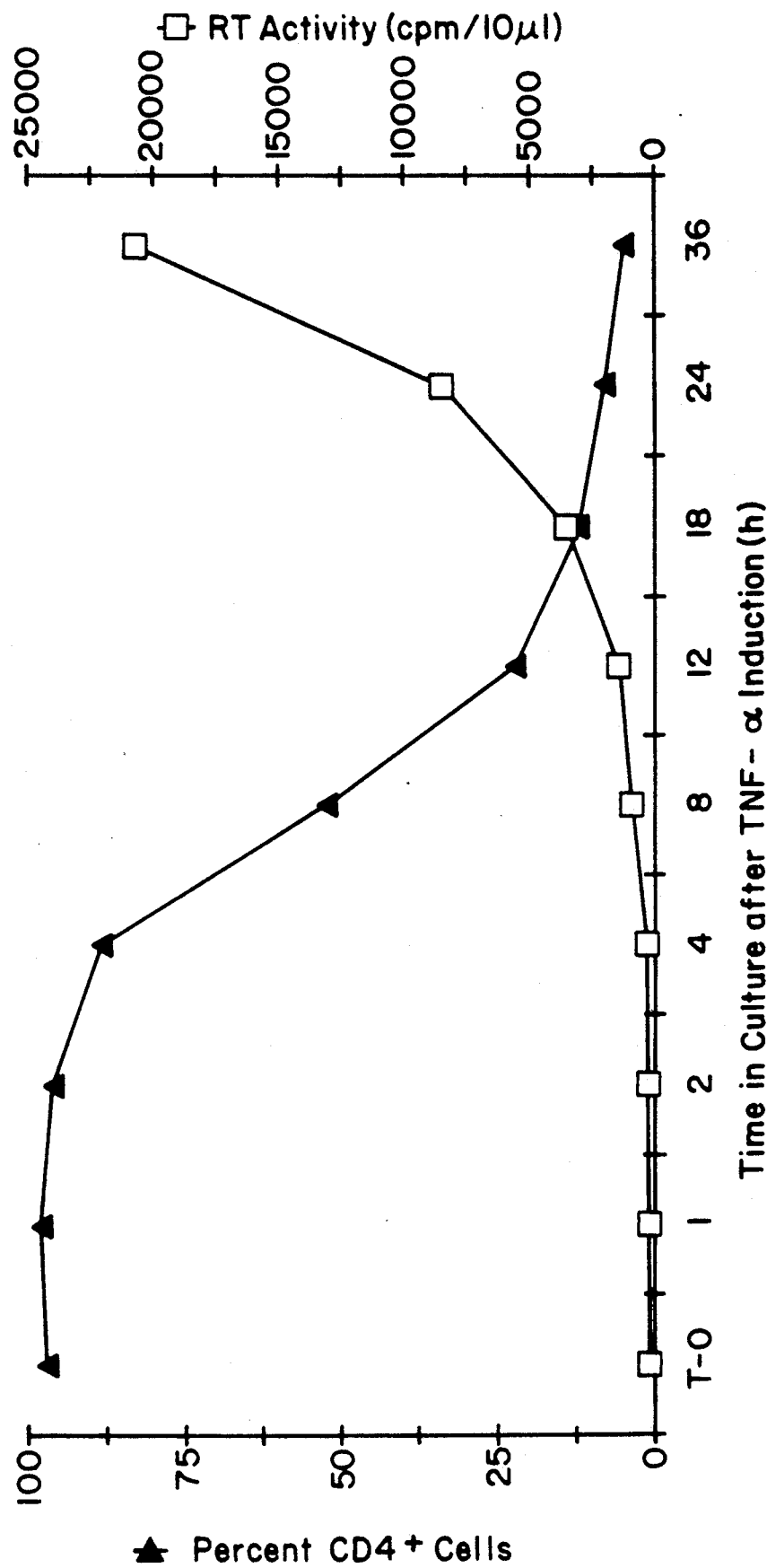
FIG. 6 demonstrates the surface CD4 expression by uninduced and TNF-α-treated OM-10.1 and HL-60 cells. (A1, A2, A3 and A4) A comparison of CD4 surface expression by OM-10.1 and HL-60 cells during the kinetic course of TNF-α treatment. Histogram profiles from flow cytometric analysis are presented and the level of surface CD4 expression is determined by the relative degree of log fluorescence intensity (abscissa of each histogram). (B) The kinetic association between TNF-α-induced down-modulation of surface CD4 on OM-10.1 cells and the rise of RT activity in the culture supernatants. The percentage of CD4+ cells was determined at each time point by gating in flow cytometry against a negative control (CD8) peak. RT activity is reported as cpm/10 μl of assay reaction mixture. (C1 and C2) Northern blot analysis of 10 μg total RNA from OM-10.1 and HL-60 cells for CD4-specific mRNA during a time course of TNF-α treatments. The anti-CD4 antibody used in these studies recognizes an epitope not involved in HIV-1 gp120 interactions and, therefor the loss of reactivity with TNF-α-induced OM-10.1 cells is due to a true loss of surface CD4 expression.

During TNF-α induction of OM-10.1 cultures, an inverse kinetic relationship was observed between the expression of surface CD4 and HIV-1 associated RT activity (FIG. 6B). A reduction in the percentage of CD4+ OM-10.1 cells occurred within 4 h of TNF-α addition and declined rapidly to <5% by 24 to 36 h. Inversely, HIV-1 expression by TNF-α-treated OM-10.1 cells was detectable in culture supernatants at 8 h and RT activity continued to rise for the remainder of the 36-h kinetic study (FIG. 6B). Because the anti-CD4 monoclonal antibody used in analysis, OKT4, defines a CD4 epitope not obstructed by HIV-1 gp 120 binding (Hoxie et al., 1986, Science (Wash, D.C.) 234:1123-1127), HIV-1 activation from OM-10.1 cells results in a true loss of surface CD4 expression.

The mechanism of CD4 down-modulation in TNF-α-treated OM-10.1 cultures was not due to a reduction in CD4 mRNA (FIGS. 6C1 and C2). OM-10.1 and HL-60 cells were treated with TNF-α for varying lengths of time and then 10 μg total RNA from these cultures was analyzed for the level of CD4-specific mRNA. After ethidium bromide staining, confirmation of the RNA quantity and integrity was obtained by UV visualization of the ribosomal bands. As shown in FIGS. 6C1 and C2, OM-10.1 cells transcribed equivalent amounts of CD4-specific mRNA, as compared with HL-60 cells, and the levels did not decline during the course of TNF-α treatment. The possibility that HIV-1 expression caused a shedding of surface CD4 was ruled out by an ELISA for soluble CD4 in which both TNF-α-treated OM-10.1 and HL-60 culture supernatants were negative. Furthermore, the continued presence of intracellular CD4 protein in OM-10.1 cells was verified by immunoblot analysis, even after 36 h of TNF-α treatment. These results clearly indicated that surface CD4 down-modulation in HIV-1-expressing OM-10.1 cells involved intracellular complexing.

Example 3

Accumulation of HIV-1 RNA in OM-10.1 and U1 cell lines

The accumulation of HIV-1 RNA after induction with TNF-α or PMA was evaluated in OM-10.1 and U1 [JI 140:1117, 1988] cell lines.

Figure 5:
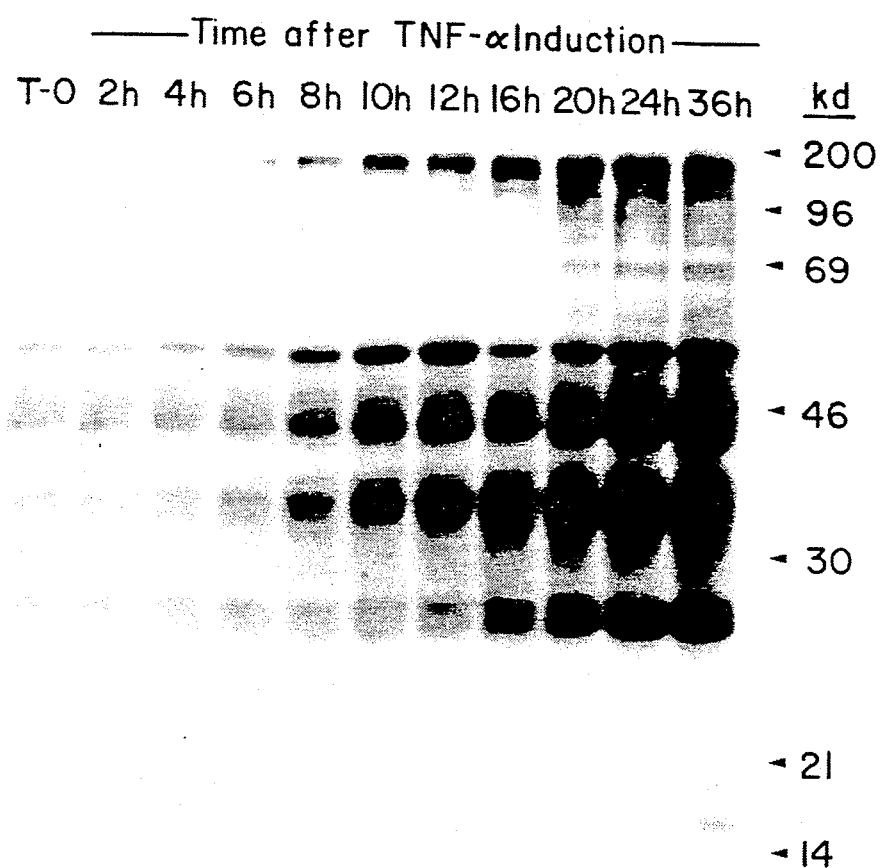
FIG. 5 shows the kinetic production of all major HIV-1 viral proteins after the induction of OM-10.1 cells with TNF-α.

In the OM-10.1 cell line, HIV-1 induction occurred at the RNA level by 4 hours and RNA continued to accumulate through the course of the culture (FIGS. 4A-D). With U1 cells, evidence of viral induction occurred much later and to a lesser extent than with OM-10.1 cells. In OM-10.1 cultures, HIV-1 proteins were observed to appear at 6 hours and continued to increase with all major viral proteins being observed (FIG. 5). In addition to the ability to maintain surface DC4 expression, from the direct comparison of OM-10.1 and U1, it is clear that OM-10.1 is a better model of HIV-1 latency (FIG. 4).

Example 4

Molecular Association Between HIV-1 gp 160/120 and CD4

In TNF-α-treated OM-10.1 cells, a direct correlation was observed between the intracellular level of HIV-1 gp160/120 and the surface expression of CD4. By immunoblot analysis (FIG. 5), HIV-1 proteins, including gp160/120, were weakly detected in unstimulated CD4+ OM-10.1 cells. However, the induced expression of HIV-1 gp160/120 was evident in OM-10.1 cells after the first 4 to 6 h of TNF-α treatment (FIG. 5) and was coincident with the observed surface CD4 down-modulation. Prolonged TNF-α treatment of OM-10.1 cells resulted in the accumulation of all HIV-1 proteins and a complete absence of surface CD4 during the 36-h induction period. Because of the observed temporal association between the production of HIV-1 gp160/120 and the down-modulation of surface CD4, verification that intracellular complexing of these proteins was a contributing factor in the CD4 down-modulation of TNF-α treated OM-10.1 cultures was attempted.

By immunoprecipitating OM-10.1 lysates with an anti-CD4 monoclonal antibody (OKT4) and then immunoblotting for associated HIV-1 proteins (FIG. 7), an intracellular HIV-1 gp160/120-CD4 complex was revealed at time points following TNF-α treatment (36 h) when surface CD4 was completely absent from these cells. In this combined procedure, the HIV-1 gp160/120 band was a specific product of the anti-CD4 immunoprecipitation because no other HIV-1 proteins were detected by immunoblotting with pooled AIDS sera. To verify the identification of HIV-1 gp160/120 in this procedure, the same lysates were immunoprecipitated with an anti-gp 120 monoclonal antibody and then immunoblotted with pooled AIDS sera (FIGS. 7A and B). This combination produced a strong single band of the identical electrophoretic mobility as that resolved by immunoblotting after anti-CD4 immunoprecipitation.

Example 5

Reciprocal Oscillations of CD4 and HIV-1 Expression by OM-10.1 Cells

Figure 8A:
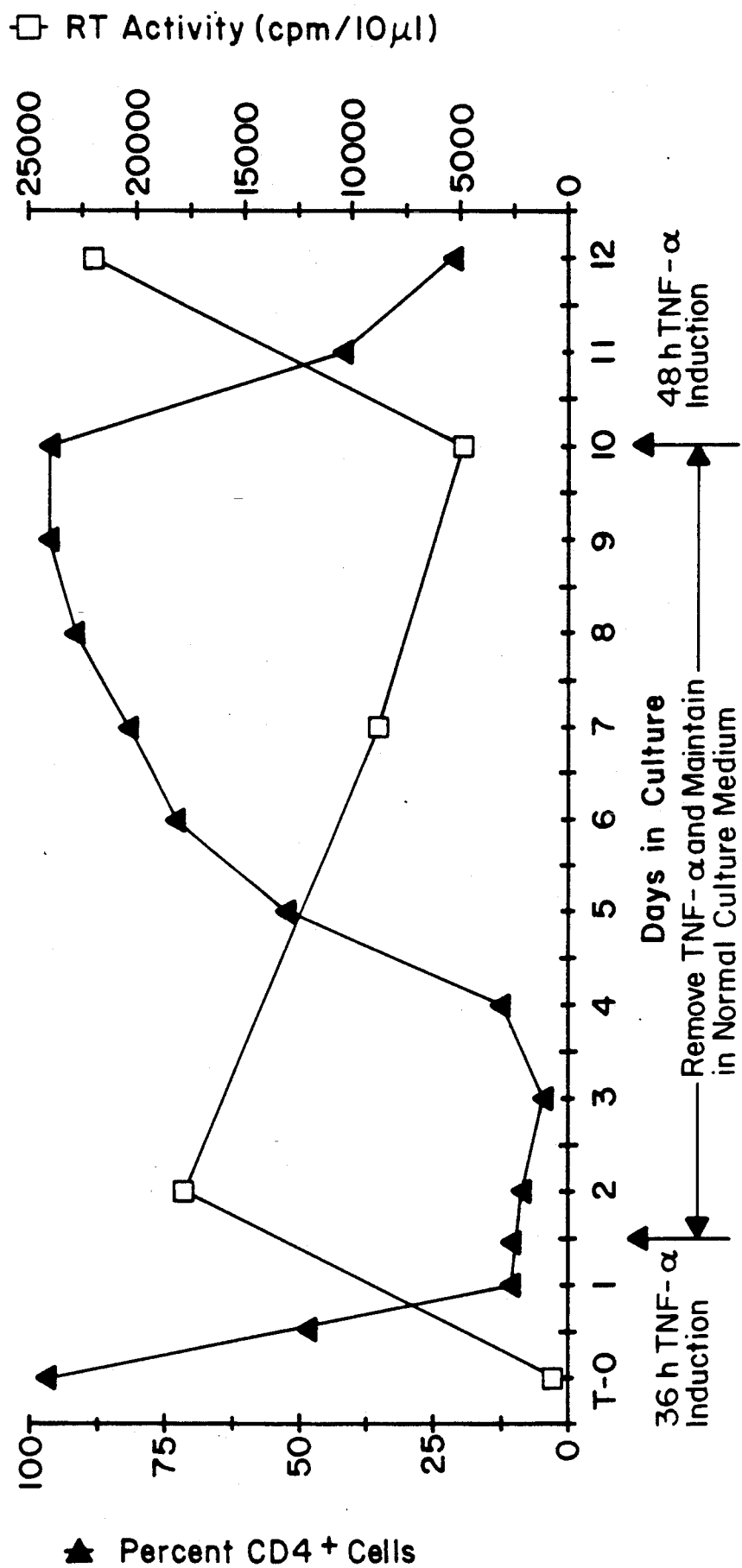
FIG. 8 demonstrates the oscillation of HIV-1 production and CD4 expression by OM-10.1 cells dependent upon external stimuli. (A) OM-10.1 cells were cultured in the presence of TNF-α for 36 h and, characteristically, this resulted in induction of HIV-1 (as measure by RT activity of culture supernatants) and down-modulation of surface CD4. After 36 h, TNF-α was removed and the cells were maintained in normal medium. HIV-1 expression slowly declined and CD4 surface expression returned after an initial lag period. When the same OM-10.1 culture was again exposed to TNF-α treatment (at Day 10), the same sequence of event occurred. (B) OM-10.1 cells were treated for 36 h with TNF-α after which the cells were placed into medium, medium containing protein kinase inhibitors (H7 or HA1004), or continued TNF-α treatment. The cultures were monitored for CD4 surface expression, as a measure of HIV-1 activation, over a period of six days.

To further confirm that the state of viral activation was controlling surface HIV-1 receptor expression in these chronically infected cells, OM-10.1 cultures were first treated with TNF-α for 36 h so that maximal CD4 down-modulation and HIV-1 activation occurred. TNF-α was then removed and the OM-10.1 cells were maintained in normal culture medium and monitored for an additional 10 days (FIG. 8A). Three days after the removal of TNF-α, CD4 surface expression could again be detected on OM-10.1 cells as supernatant RT activity began to decline, without apparent cytopathicity. By day 6 after TNF-α removal, surface CD4 expression returned to near normal levels concurrent with a continued reversion of HIV-1 to an inactive state as evidence by the decline of RT activity. These OM-10.1 cultures regained the resting phenotype (>90% CD4+ cells) by day 9 and were again induced by TNF-α treatment on day 10. Upon restimulation, down-modulation of surface CD4 and the rise of culture supernatant RT activity occurred with similar kinetics as in the first induction period.

It had been previously observed that inhibition of protein kinase activity completely blocked TNF-α-induced HIV-1 activation in OM-10.1 cultures. Therefore, the involvement of intracellular protein kinase activity in maintaining HIV-1 activation and depressed CD4 expression during the 4- to 5-day period after the removal of the TNF-α stimulus was investigated. OM-10.1 cells were treated for 36 h with TNF-α, washed, and then placed back into medium alone or into medium containing the protein kinase inhibitor, H7, or an analog without inhibitory activity, HA1004 (Hidaka et al., 1984, Biochemistry 23:5036–5041). These cells were then monitored for the reappearance of CD4 over several additional days in culture (FIG. 8B). In cells placed back into medium, a 4 to 5 day period before the return of surface CD4 to pretreatment levels was again observed. However, the addition of H7 dramatically altered the kinetics of CD4 return. Pretreatment CD4 levels were found to return with enhanced kinetics (2 days) after TNF-α removal. The pattern of CD4 return in HA1004-treated OM-10.1 cells was identical to that of the medium culture. Furthermore, CD4 remained undetectable on OM-10.1 cells when maintained in the continued presence of TNF-α during the 6 day culture.

Example 6

Differentiation of OM-10.1 Cells

Figure 9:
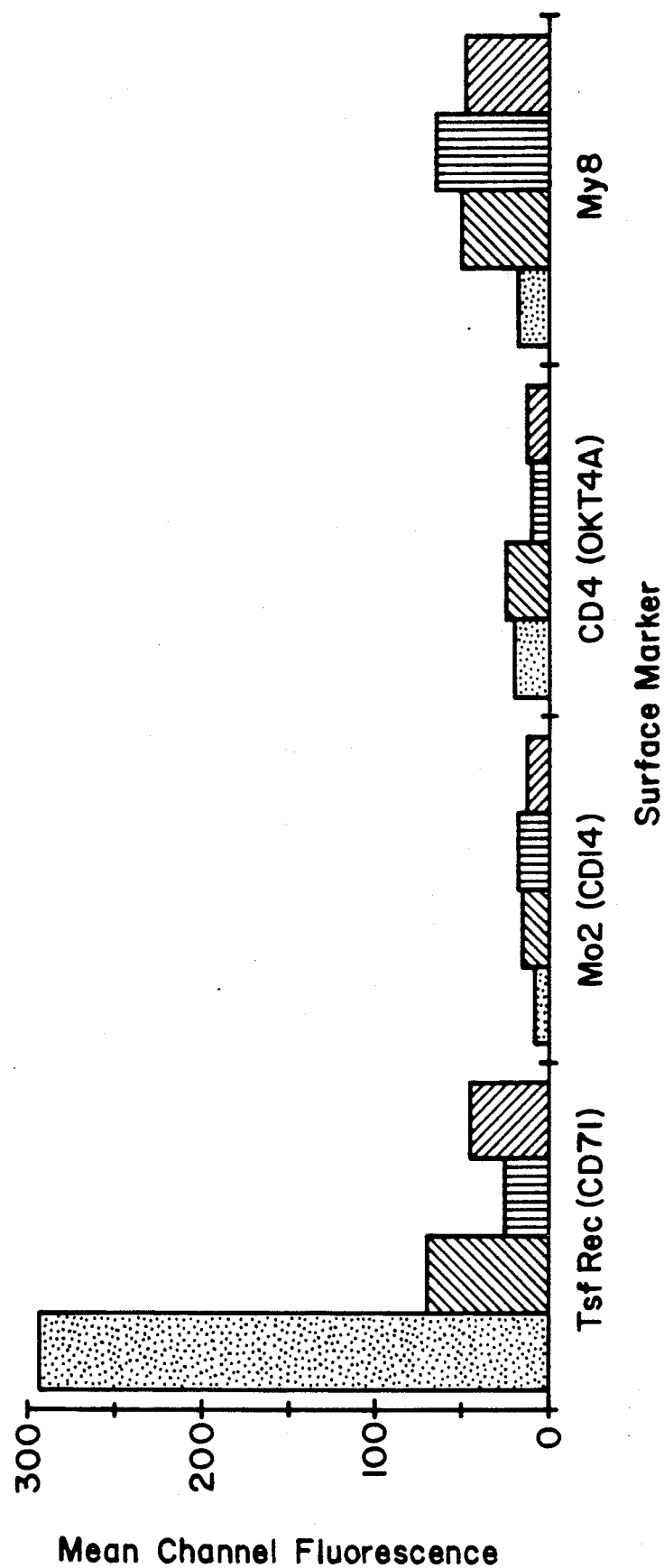
FIG. 9 illustrates the differentiation of OM-10.1 into several terminal hematopoietic phenotypes as determined by the modulation of cell surface markers (CD71, CD14, CD4 and My8).

OM-10.1 is a hematopoietic progenitor cell of the promyelocytic lineage. These HIV-1 infected cells retained their ability to differentiate into several terminal phenotypes as evidenced by a reduction of CD71 and an increase of My8 and CD14 surface markers (see FIG. 9). OM-10.1 cultures were established at a density of $5 \times 10^5$ cells per ml to assess the cellular responses to differentiating agents. Final concentrations for each agent were: dimethyl sulfoxide (Fisher Scientific, Fair Lawn, N.J.)=1.2%; retinoic acid (Sigma)=1 μM; and sodium butyrate (Sigma)=0.5 mM. Medium control cultures were also established and maintained under indentical conditions. After a 72 hour incubation period, cells from these cultures were examined for morphologic and phenotypic evidence of differentiation as described above. Thus infected OM-10.1 cells can be differentiated and then used as infected models for several terminal phenotypes. In addition, the relationships between differentiation and HIV-1 expression can be addressed.

Example 7

Superinfection of OM-10.1 Cells

To determine if OM-10.1 cells can be superinfected with HIV-1, the cells were tested for the accumulation of unintegrated HIV-1 DNA. Three forms of HIV-1 DNA accumulate. These include a linear copy of the viral genome with long terminal repeats (LTRs) and two covalently closed circular forms. Cell lysates of OM-10.1 were tested for the presence of two-LTR circular forms as a specific marker of acute superinfection.

Polymerase chain reaction (PCR) analysis was carried out on whole-cell lysates of OM-10.1 cells, using primers binding to the U5 and U3 regions of the LTR as described in Besansky et al (1991, J Virology, 65:2695–2698).

Briefly, cells were washed twice with phosphate-buffered saline and suspended in PCR lysis buffer. After lysis, PCR was performed with 25 μl of lysate and 100 ng of each primer for 35 cycles at 94° C. for 1 min, 61° C. for 1 min, and 72° C. for 30 sec as described (Saiki et al., 1988, Science 239:487–491). The 5' two-LTR primer binds positions 366 to 585 of HXB2 (Ratner et al., 1985, Nature (London) 313:277–284), the 3' primer binds positions 9170 to 9151, and the two-LTR probe binds positions 591 to 620. A region of the gag was amplified using primers SK38 and SK39 (Ou et al., 1988, Science 239:295–297) as a positive control for the presence of viral DNA.

Figure 10:
FIG. 10 shows the results of polymerase chain reaction (PCR) analysis of two-LTR circular unintegrated HIV-1 DNA during acute and chronic infections. Cell lines tested include acutely infected A3.01 T-lymphocytes (Folks et al., 1985, Proc. Natl. Acad. Sci. USA 82:4539–4543), acutely infected peripheral blood leukocytes (PBL's), and chronically infected OM-10.1 promyelocytes.

The amplification products were analyzed by agarose gel electrophoresis and Southern blot hybridization to a 5'$^{32}$P-labeled two-LTR probe or to gag probe SK19 (Ou et al., 1988, Science 239:295–297). Amplification products of the expected molecular size were obtained from OM-10.1. A high copy number of unintegrated HIV-1 DNA was detected in OM-10.1 cultures as evidenced in FIG. 10.

Figure 11A:
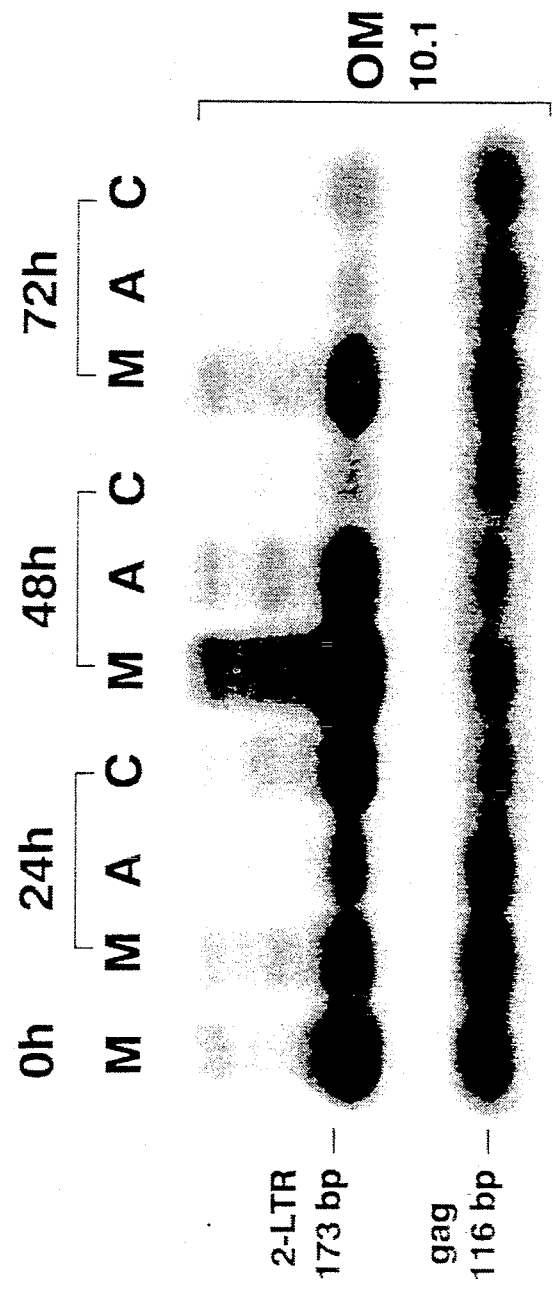
FIG. 11 shows the effect of AZT or sCD4 on accumulation of two-LTR circles in OM-10.1 cells. (A) Untreated lane=M, AZT-treated lane=A, and sCD4 treated lane=C. (B) AZT removed lane=PA, untreated cultures lane=M. The modulation of unintegrated HIV-1 DNA dependent upon treatment with inhibitors of acute infection verifies that superinfection is an acute, continuous process in the CD4+ OM-10.1 cell line.
Figure 11B:
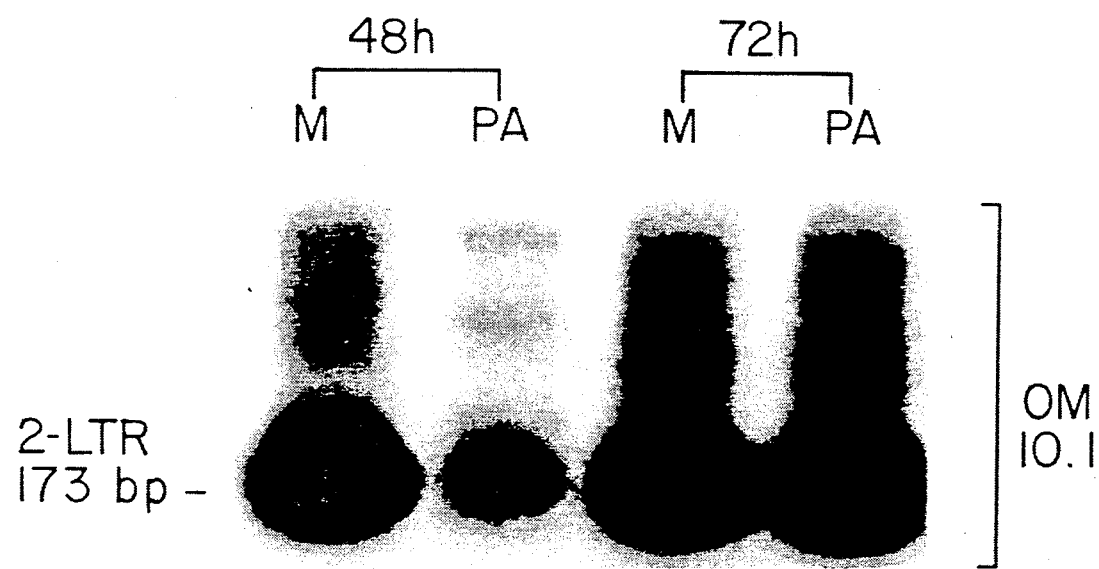

To determine whether the unintegrated DNA was due to acute reinfection and reverse transcription of intracellular viral transcripts, culture of OM-10.1 were maintained in the presence or absence of either AZT (a viral reverse transcriptase inhibitor, Burroughs Wellcome) or a sCD4 (which blocks viral binding and acute infection, Genentech) at 10 or 20 μg/ml of medium, respectively. PCR analysis was performed on samples removed at setup and at 24-h intervals (FIG. 11). Within 72 h, both treatments substantially reduced the level of the HIV-1 two-LTR DNA circles in OM-10.1 with no discernible effects on cell viability, efficiency of amplification or toal detectable HIV-1 DNA. Thus, the presence of unintegrated HIV-1 DNA in these cultures reflects an acute superinfection by progeny virions mediated through surface CD4 binding and penetration.

The length of time required to restore unintegrated viral DNA to pretreatment levels was determined by washing AZT-treated OM-10.1 cells and resuspending them in medium alone. Samples were removed at zero hour and at 24-h intervals and subjected to PCR analysis. The results were compared with untreated cultures (see FIG. 11B). By 72 h post-AZT treatment, two-LTR circles had returned to pretreatment levels, implying that reinfection is a continuous process.

Statement of Deposit

The cell line OM-10.1 was deposited on Aug. 1, 1991 under the terms of the Budapest Treaty at the American Type Culture Collection (Rockville, Md.). OM-10.1 has been assigned the ATCC accession number CRL 10850.

The deposited cell line will be available during the pendency of the present patent application and will be replaced if it should become nonviable or non-replicative. Further, upon issuance of a patent on the present application, all restrictions as to public availability of the culture deposit will be irrevocably removed and the culture deposit will be replaced should the depository be unable to distribute the sample upon a proper request, during the period that extends thirty years from the date of the deposit, or the period of the enforceable life of the patent, or the period of five years after the last public request for the deposit, whichever period is longest.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A purified and isolated cell line which is derived from a hematopoietic cell and wherein the cells of said cell line are CD4+ and comprise a latent HIV-1 provirus.

2. The cell according to claim 1 which is a pluripotent progenitor stem cell.

3. The cell according to claim 1 which is a promyelocyte.

4. The cell according to claim 2 which is ATCC CRL 10850.

5. The cell according to claim 1 which is a neutrophil, basophil or eosinophil.

6. The cell according to claim 1 which is superinfectable.

7. A rapid method of identifying anti-HIV-1 agents comprising contacting said cells according to claim 1 with said agent and detecting the presence or absence of cell death.

8. A method of identifying agents which prevent HIV-1 activation comprising contacting said cells according to claim 1 with said agent and an HIV-1 activation stimulus, and detecting the presence or absence of HIV-1 activation.

9. The method according to claim 8 wherein said stimulus is TNF-α or a phorbol ester.

10. A purified and isolated cell line which is derived from a hematopoietic cell and wherein the cells of said cell line are CD4+ and comprise a latent HIV-1 provirus and at least one copy of an unintegrated HIV-1 DNA.

* * * * *